US012551665B2

(12) United States Patent
Osypka

(10) Patent No.: US 12,551,665 B2
(45) Date of Patent: Feb. 17, 2026

(54) DEFLECTABLE PEEL AWAY SHEATH

(71) Applicant: Oscor Inc., Palm Harbor, FL (US)

(72) Inventor: Thomas P. Osypka, Palm Harbor, FL (US)

(73) Assignee: Greatbatch Ltd., Clarence, NY (US)

( * ) Notice: Subject to any disclaimer, the term of this patent is extended or adjusted under 35 U.S.C. 154(b) by 961 days.

(21) Appl. No.: 17/735,895

(22) Filed: May 3, 2022

(65) Prior Publication Data

US 2022/0347437 A1 Nov. 3, 2022

Related U.S. Application Data

(60) Provisional application No. 63/183,370, filed on May 3, 2021.

(51) Int. Cl.
*A61M 25/06* (2006.01)
*A61M 25/01* (2006.01)

(52) U.S. Cl.
CPC .... *A61M 25/0668* (2013.01); *A61M 25/0136* (2013.01); *A61M 25/0147* (2013.01)

(58) Field of Classification Search
CPC ...... A61M 25/0668; A61M 2025/0188; A61M 2025/0161; A61M 25/0147; A61M 25/0136
USPC .................................................... 604/164.05
See application file for complete search history.

(56) References Cited

U.S. PATENT DOCUMENTS

| | | | | |
|---|---|---|---|---|
| 6,562,049 B1 * | 5/2003 | Norlander | A61M 25/0075 606/108 |
| 6,979,319 B2 | 12/2005 | Manning et al. | |
| 7,117,039 B2 | 10/2006 | Manning et al. | |
| 7,697,996 B2 | 4/2010 | Manning et al. | |
| 8,126,570 B2 * | 2/2012 | Manning | A61M 25/0668 607/119 |
| 10,035,000 B2 * | 7/2018 | Bednarek | A61B 5/287 |
| 2005/0090779 A1 * | 4/2005 | Osypka | A61M 25/0662 604/160 |
| 2006/0155247 A1 * | 7/2006 | Lampropoulos | A61M 39/223 251/304 |
| 2009/0030374 A1 * | 1/2009 | Osypka | A61M 25/0668 604/164.05 |
| 2009/0192495 A1 * | 7/2009 | Ostrovsky | A61M 25/0138 604/528 |

(Continued)

*Primary Examiner* — Jason E Flick
*Assistant Examiner* — Isabella S North
(74) *Attorney, Agent, or Firm* — Michael F. Scalise

(57) ABSTRACT

A deflectable vascular peel away introducer assembly includes an elongated sheath including opposed proximal and distal end portions and at least two axial lumens extending therethrough. The elongated sheath includes at least two axially extending lines of weakness. A movable pull-wire is positioned within one of the two axial lumens. The movable pull-wire is anchored to the distal end portion of the elongated sheath to deflect a distal tip of the distal end portion of the elongated sheath. A method for deflecting and removing a vascular peel away assembly includes turning a deflection knob which causes deflection of a softer distal end portion of an elongated sheath along a primary curve. The method includes splitting spreadable handles at a proximal end portion of the elongated sheath along peel lines. The deflection can be 45 degrees or more.

23 Claims, 13 Drawing Sheets

(56) References Cited

U.S. PATENT DOCUMENTS

| | | | | |
|---|---|---|---|---|
| 2012/0136350 | A1* | 5/2012 | Goshgarian | A61B 18/1492<br>606/41 |
| 2016/0058975 | A1* | 3/2016 | Kimmel | A61M 25/0147<br>600/411 |
| 2016/0279423 | A1* | 9/2016 | Kelly | A61M 25/0136 |
| 2017/0113017 | A1* | 4/2017 | Zhang | A61M 25/01 |
| 2017/0143940 | A1* | 5/2017 | Flygare | A61M 25/0136 |
| 2020/0061340 | A1* | 2/2020 | Mixter | A61M 25/0136 |
| 2020/0360141 | A1* | 11/2020 | Stappenbeck | A61F 2/9517 |

* cited by examiner

Fig. 7
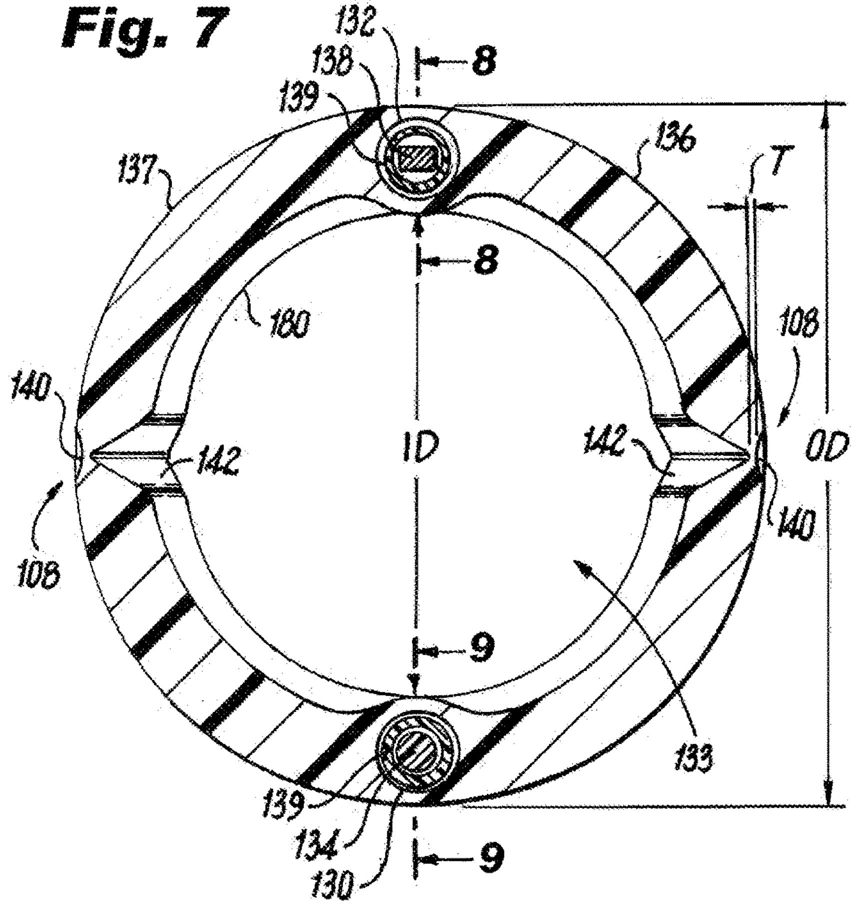
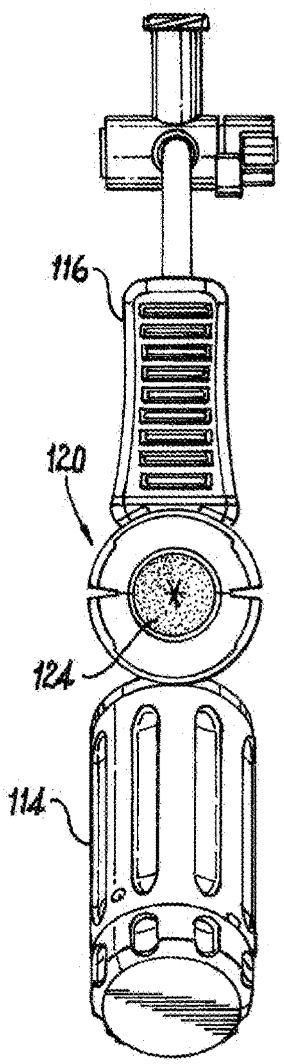
Fig. 6
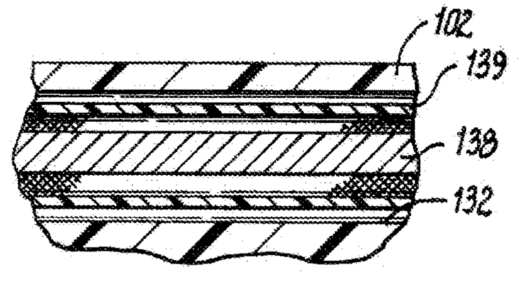
Fig. 8
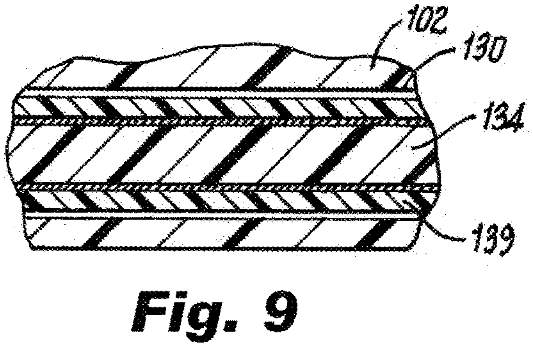
Fig. 9

DEFLECTABLE PEEL AWAY SHEATH

CROSS-REFERENCE TO RELATED APPLICATION

This application claims the benefit of priority to U.S. Provisional Patent Application Ser. No. 63/183,370 filed May 3, 2021, the disclosure of which is herein incorporated by reference in its entirety.

BACKGROUND OF THE INVENTION

1. Field of the Invention

The subject technology relates to a vascular introducer, and more particularly, to a vascular introducer having a peel-away sheath with opposed peel lines.

2. Description of Related Art

Introducer devices have been employed for inserting catheters, guide wires, leads and the like into patients. A typical procedure provides for insertion of a dilator or needle encased within a sheath into the vasculature of a patient. After insertion, the dilator or needle may be removed leaving the sheath protruding from the patient's vein. The sheath is then removed. To remove the sheath, the sheath may be split or peeled away along two diametrically opposed score lines. Alternatively, the sheath may be slit open using a specialized cutting blade.

These kind of introducer devices have been, in particular, very useful for introducing cardiac pacing and defibrillation leads into the vascular system. There may be, however, drawbacks associated with the current peelable sheaths. For example, such introducers may have limitations when exact navigation and positioning of leads or devices inside the heart chamber are required. In such cases, a steerable guiding catheter would be preferred as an insertion tool (like Oscor Destino™), which comes with a deflectable distal curve section. Such steerable guiding catheters, however, are not typically usable for the implantation and positioning of implantable cardiac leads, since such leads feature a larger proximal connector which requires the delivery system to be "peeled" once the lead is implanted. For example, placing leads inside the HIS-Bundle of the right ventricular wall would require such peel away sheath and steering capability.

There is a need, therefore, for an improved peel away sheath which allows the distal section of the sheath to be deflected, is easy to navigate as a deflectable guiding sheath, is efficient to fabricate and easy to use as well as assuring adequate separation.

SUMMARY

A deflectable vascular peel away introducer assembly includes an elongated sheath including opposed proximal and distal end portions and at least two axial lumens extending therethrough. The elongated sheath includes at least two axially extending lines of weakness. A movable pull-wire is positioned within one of the two axial lumens. The movable pull-wire is anchored to the distal end portion of the elongated sheath to deflect a distal tip of the distal end portion of the elongated sheath.

In certain embodiments, the elongated sheath includes a tubular sheath wall. The axial lumen with the movable pull-wire can be embedded within the sheath wall. The movable pull-wire can be anchored within the one of the at least two axial lumens with epoxy at the distal end portion of the elongated sheath. The elongated sheath can include a tubular sheath wall. A second of the at least two axial lumens is defined within an inner diameter of the tubular sheath wall. The proximal end portion of the elongated sheath can be stiffer and less flexible than the distal end portion of the elongated sheath. The distal end portion can include at least two softer sections with different stiffness. A first of the two softer sections can be configured and adapted to be deflected to a primary curve of predetermined Deflection Curve Diameter (DCD). A second of the two softer sections can be pre-shaped to a secondary curve. The primary curve can be longer in arc-length than the secondary curve. The elongated sheath can define a predetermined usable length (UL) extending from the proximal end portion to the distal tip of the distal end portion of the sheath. The UL can range from 30 cm to 70 cm. The elongated sheath can define a circumference and the two lines of weakness are diametrically opposed to one another across the elongated sheath. The elongated sheath can define a longitudinal axis. The lines of weakness can include longitudinally extending score lines for dividing the sheath along the longitudinal axis thereof. The longitudinally extending score lines can be defined opposite from one another across an inner diameter of the elongated sheath. Each line of weakness can include an axially extending detent formed in an outer diameter surface of the elongated sheath. Each axially extending detent can be opposite from a respective one of the longitudinally extending score lines across a sheath wall.

In certain embodiments, the deflectable vascular peel away introducer assembly further includes a hub positioned at the proximal end portion of the sheath. The hub can include a pair of diametrically opposed spreadable handles divided by hub lines of weakness. The deflectable vascular peel away introducer assembly can include a hemostatic valve positioned between the spreadable handles. The spreadable handles can be configured and adapted to split along the hub lines of weakness and facilitate separating the elongated sheath along the lines of weakness. One of the spreadable handles can include a side port conduit extending therefrom. The side port conduit can have a two-way or three-way stop cock. The side port conduit can be in fluid communication with one of the at least two axial lumens. One of the spreadable handles can include a deflection knob operatively connected to a proximal end of a pull wire. A distal end of the pull wire can be anchored to the distal end of the elongated sheath via a pull wire anchor ring. The deflection knob can be rotated relative to the spreadable handle. The distal tip of the distal end portion of the elongated sheath can be configured to deflect. The assembly can include a memory wire positioned within a second of the at least two axial lumens. The memory wire can be configured and adapted to assist with straightening a distal end portion of the elongated sheath after deflection.

In accordance with another aspect, a method for deflecting and removing a vascular peel away assembly includes turning a deflection knob which causes deflection of a softer distal end portion of an elongated sheath along a primary curve. The method includes splitting spreadable handles at a proximal end portion of the elongated sheath along peel lines. The deflection can be 45 degrees or more.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the steerable intravascular catheter of the subject invention appertains will readily understand how to make and use the device without undue experimentation, preferred embodiments thereof will be described in detail herein below with reference to certain figures, wherein:

FIG. 6 is a proximal end elevation view, showing two spreadable handles separated by a hemostatic valve and hub;

FIG. 7 is a schematic cross section view of the elongated sheath of FIG. 1, showing two axial lumens;

FIG. 8 is a schematic detail view of a cross-section of the elongated sheath of FIG. 1, showing a memory wire and an axial lumen;

FIG. 9 is a schematic detail view of a cross-section of the elongated sheath of FIG. 1, showing a pull wire and pull wire lumen;

DESCRIPTION OF THE EMBODIMENTS

Figure 1:
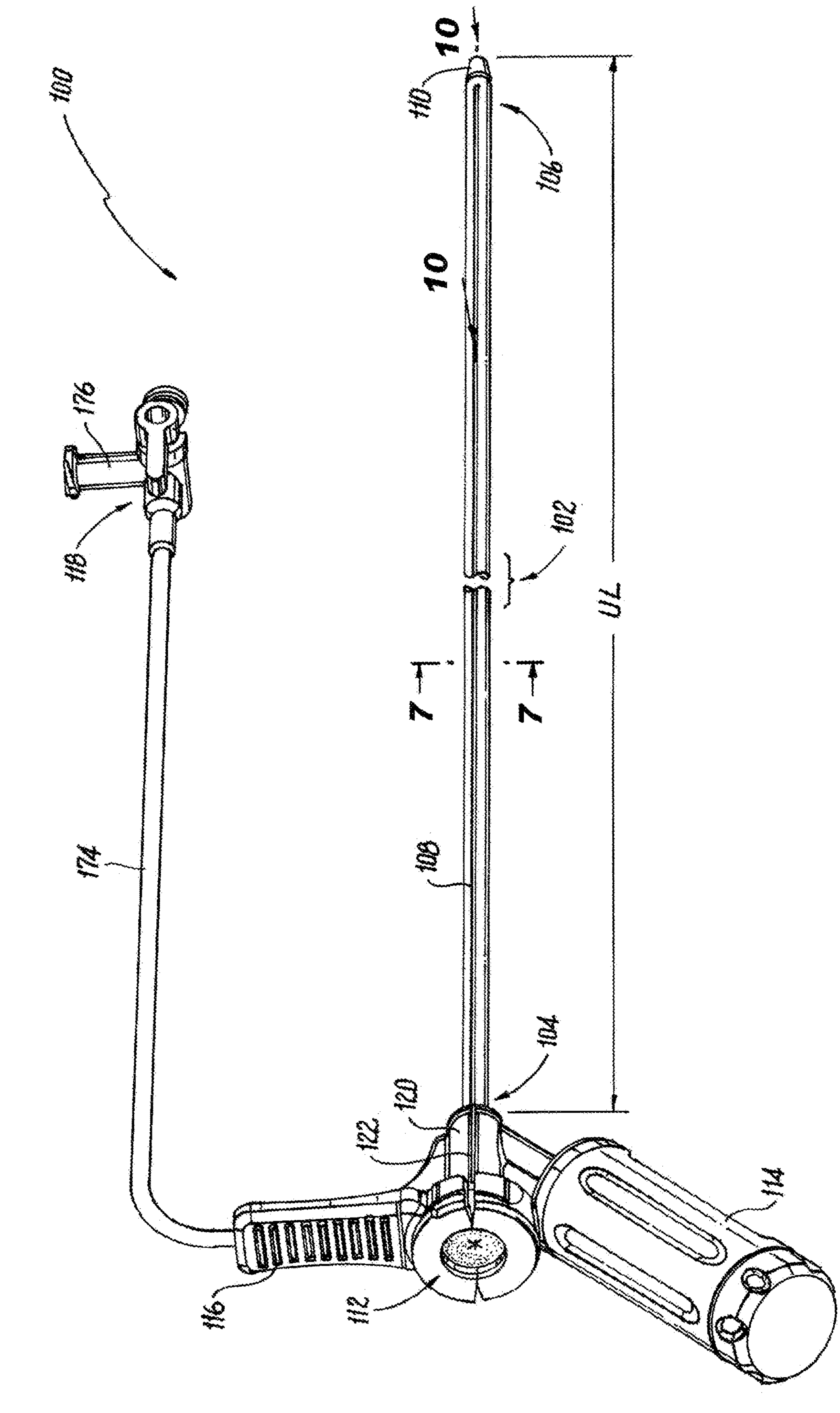
FIG. 1 is perspective view of a deflectable vascular peel away introducer assembly constructed in accordance with an embodiment of the present disclosure, showing a deflectable distal end of the sheath.

Referring now to the appended drawings, wherein like reference numerals identify similar structures or features of the subject invention, there is illustrated in FIGS. 1-26 a new and useful peel-away introducer sheath assembly constructed in accordance with a preferred embodiment of the subject disclosure and designated generally by reference numeral 100. The peel-away introducer sheath assembly 100 includes a peel-away sheath, while incorporating a deflection mechanism to deflect the distal tip of the distal portion of the elongated sheath by turning a deflection knob located on the proximal handle on the proximal end portion of the elongated sheath.

As shown in FIGS. 1-5, a deflectable vascular peel away introducer assembly 100 includes an elongated sheath 102 having opposed proximal 104 and distal 106 end portions. The elongated sheath 102 defines a longitudinal axis A and includes two axially extending lines of weakness 108. The sheath 102 can have an inner diameter (shown in FIG. 7) ranging from 8.5 French (F) to 13 F. The distal end portion 106 terminates in a distal tip 110. The distal tip 110 of the distal end portion 106 of the elongated sheath 102 is configured to deflect. The distal end portion 106 includes two softer sections with a different stiffness. A first 182 of the two softer sections is configured and adapted to be deflected to a primary curve 126 of predetermined Deflection Curve Diameter (DCD). A second 129 of the two softer sections is pre-shaped to a secondary curve 128. The DCD of primary curve 126 can have a radius of curvature that is smaller than that of secondary curve 128.

With reference now to FIG. 1, the proximal end portion 104 terminates in a proximal handle 112. The proximal handle 112 further includes a pair of spreadable handles 114 and 116, a spreadable rotating twist deflection handle 114, and a break away spreadable handle 116 connected to a side port flush 118. Spreadable handle 116 includes a sideport conduit 174 extending therefrom. The sideport conduit 174 can have a two-way or three-way stop cock 176. The sideport conduit 174 is in fluid communication with one of the two axial lumens 130, 132. The deflectable vascular peel away introducer assembly 100 includes a hub 120 positioned at the proximal end portion 104 of the sheath 102.

Figure 2:
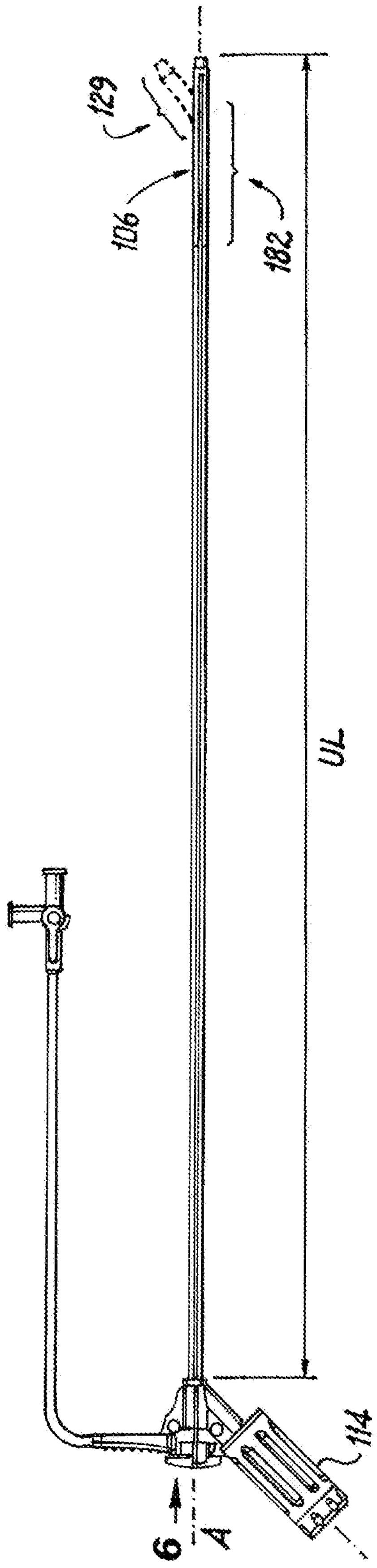
FIG. 2 is a schematic side elevation view of the deflectable vascular peel away introducer assembly of FIG. 1, showing the deflectable end portion of the elongated sheath in a non-deflected position.
Figure 3:
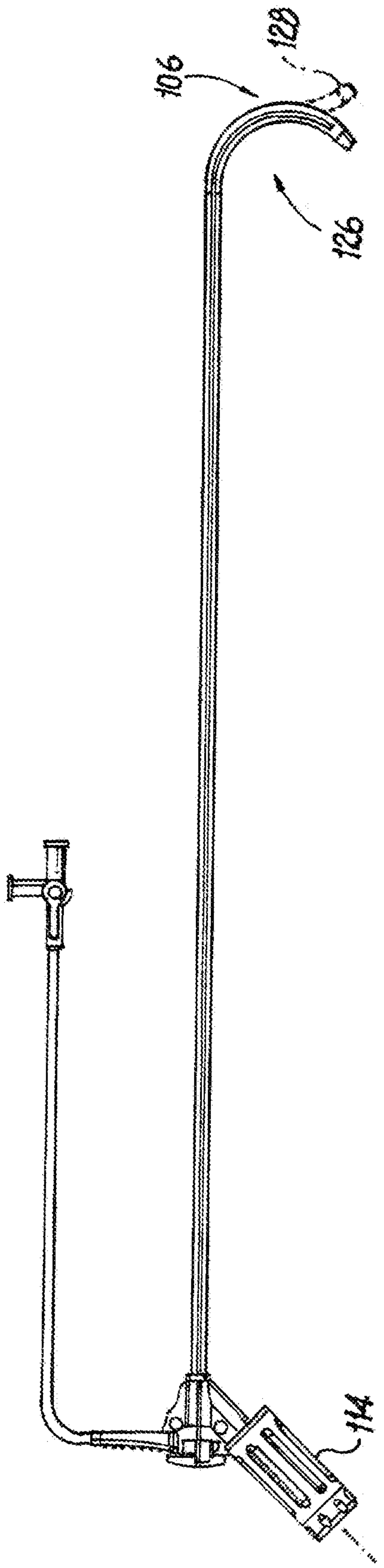
FIG. 3 is a schematic side elevation view of the deflectable vascular peel away introducer assembly of FIG. 1, showing the deflectable distal end portion of the elongated sheath in a deflected position.

As shown in FIG. 2, the first 182 of the two softer sections of the distal end portion 106 is in a non-deflected position. In FIG. 3, the first 182 of the two softer sections at the distal end portion 106 is in a deflected position. The proximal end portion 104 of the elongated sheath 102 can be stiffer and less flexible than the distal end portion 106 of the elongated sheath 102. In embodiments where the sheath includes both a primary curve 126 and a secondary curve 128 (shown schematically by broken lines in FIGS. 2-3.), the section of the sheath forming the primary curve is longer in arc-length than the section forming the secondary curve 128. In FIG. 3, while in the deflected position, distal end portion 106 forms a primary curve 126 and, optionally, secondary curve 128.

Figure 4:
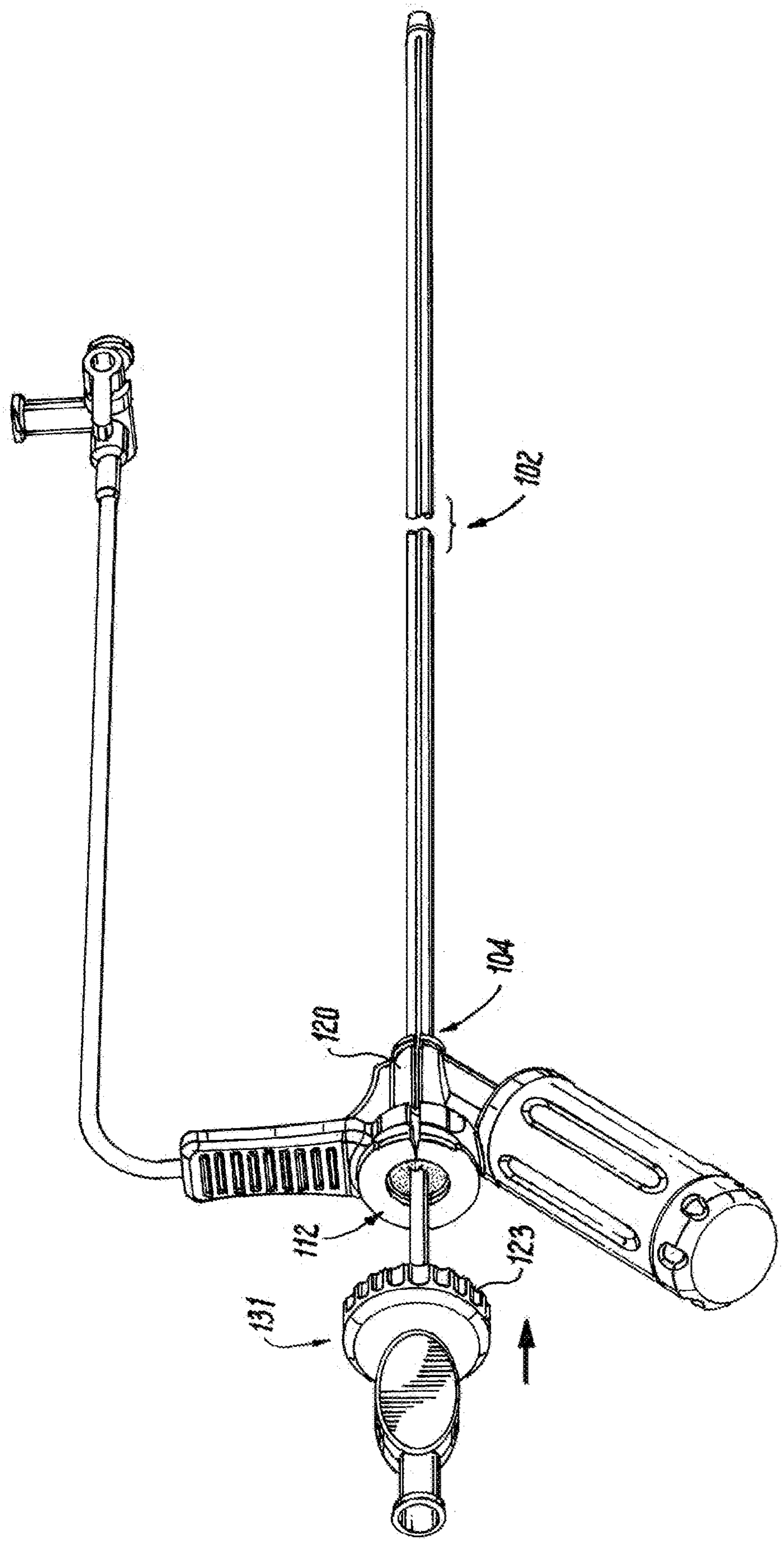
FIG. 4 is a perspective view of the deflectable vascular peel away introducer assembly of FIG. 1, showing a dilator being inserted within the elongated sheath.
Figure 5:
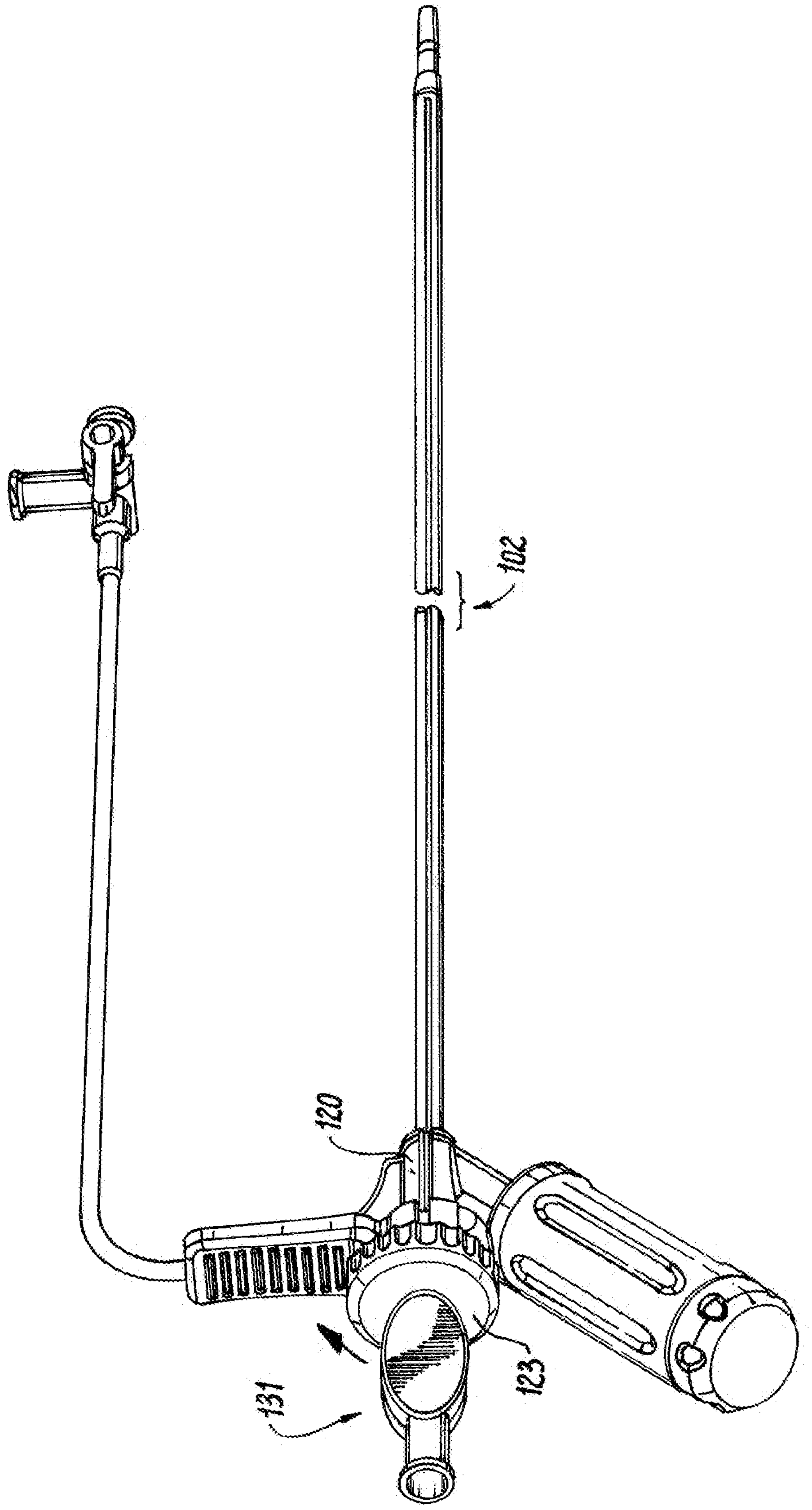
FIG. 5 is a perspective view of the deflectable vascular peel away introducer assembly of FIG. 1, showing the dilator in the inserted position

As shown in FIG. 4-6, the hub 120 is between the diametrically opposed spreadable rotating twist deflection handle 114 and the breakaway handle 116 and is divided by hub lines of weakness 122. A hemostatic valve 124 is positioned abutting a proximal end 121 of the hub 120. As shown in FIGS. 4-5, a dilator 131 is being inserted through hemostatic valve 124 and into hub 120.

As shown in FIG. 7, the elongated sheath 102 includes a tubular sheath wall 136 having an outer surface 137 defining a circumference. The two lines of weakness 108 are diametrically opposed to one another across the elongated sheath 102 forming two peel away zones. In the embodiment of FIG. 7, each line of weakness 108 includes an axially extending detent 140 formed in the outer diameter surface 137. Lines of weakness 108 include longitudinally extending narrow deep "V" score lines 142 on opposing sides of an inner diameter surface 180 for dividing the sheath 102 along the longitudinal axis A thereof. The wall thickness T where the apex of the "V" meets the detent 140 can be approximately 0.003".

Figure 10:
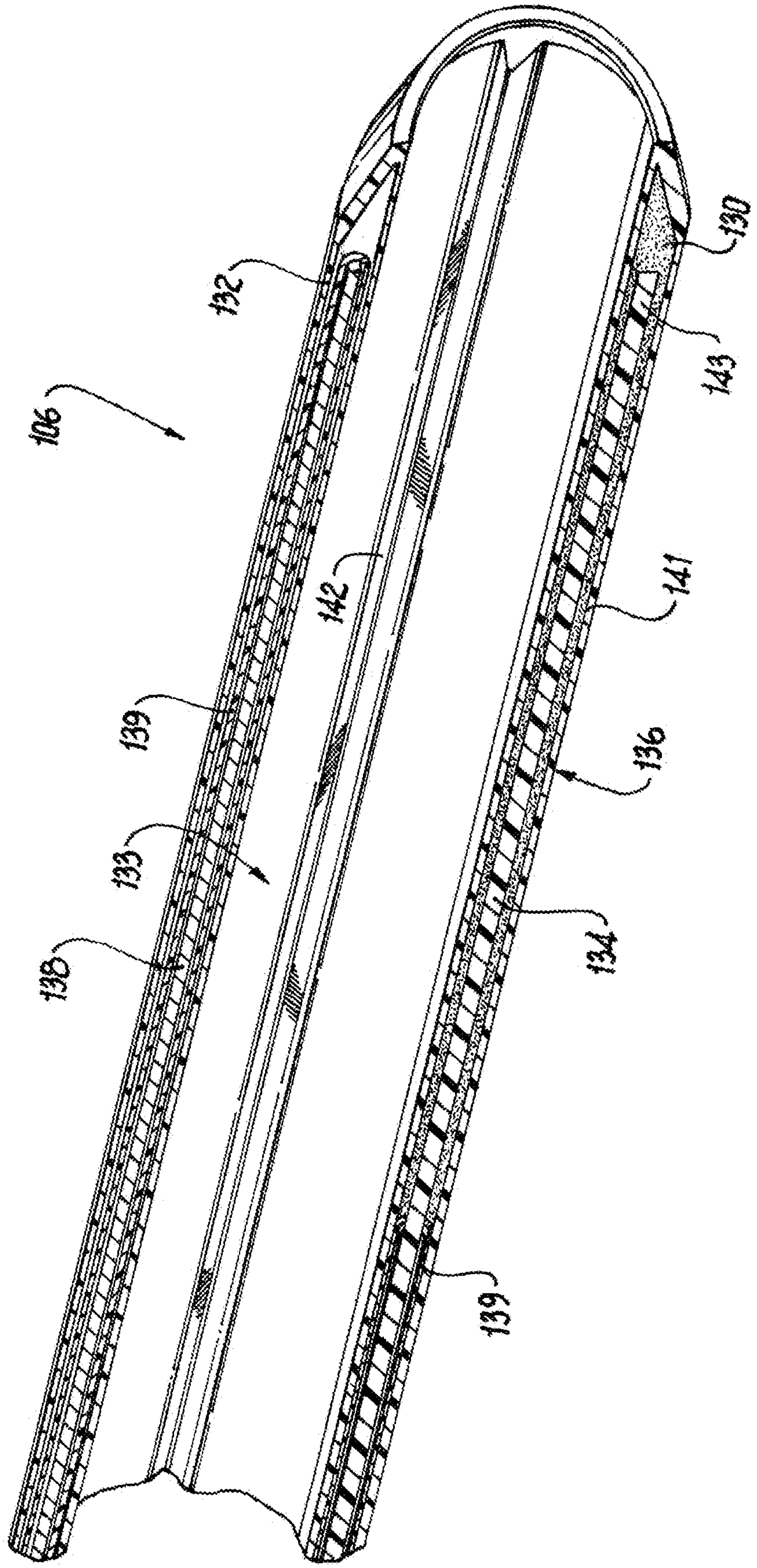
FIG. 10 is a schematic cross section view of the distal end portion of the elongated sheath of FIG. 1, showing the pull wire anchored in the pull wire lumen with adhesive.

With reference now to FIGS. 7-10, tubular sheath 136 defines an inner axial lumen 133 within an inner diameter of the sheath wall 136 to receive, for example, the dilator 131. The elongated sheath 102 has two axial lumens 130, 132 embedded in sheath wall 136. In accordance with some embodiments, each of the axial lumens 130, 132 includes braided polyimide tubing 139 nested therein. One of the axial lumens 130 has a movable pull-wire 134 positioned within the braided polyimide tubing 139. The moveable pull-wire 134 can be a Kevlar pull string which cannot push or puncture the sheath wall 136. As shown in FIG. 10, a distal end 143 of movable pull-wire 134 is anchored within lumen 130 with epoxy 141 at the distal end portion 106 of the elongated sheath 102 to deflect the distal tip 110 of the distal end portion 106 of the elongated sheath 102. Axial lumen 132 contains a rectangular memory wire 138 to assist with straightening after bending. In some embodiments, memory wire 138 can be a nitinol memory wire.

Figure 11:
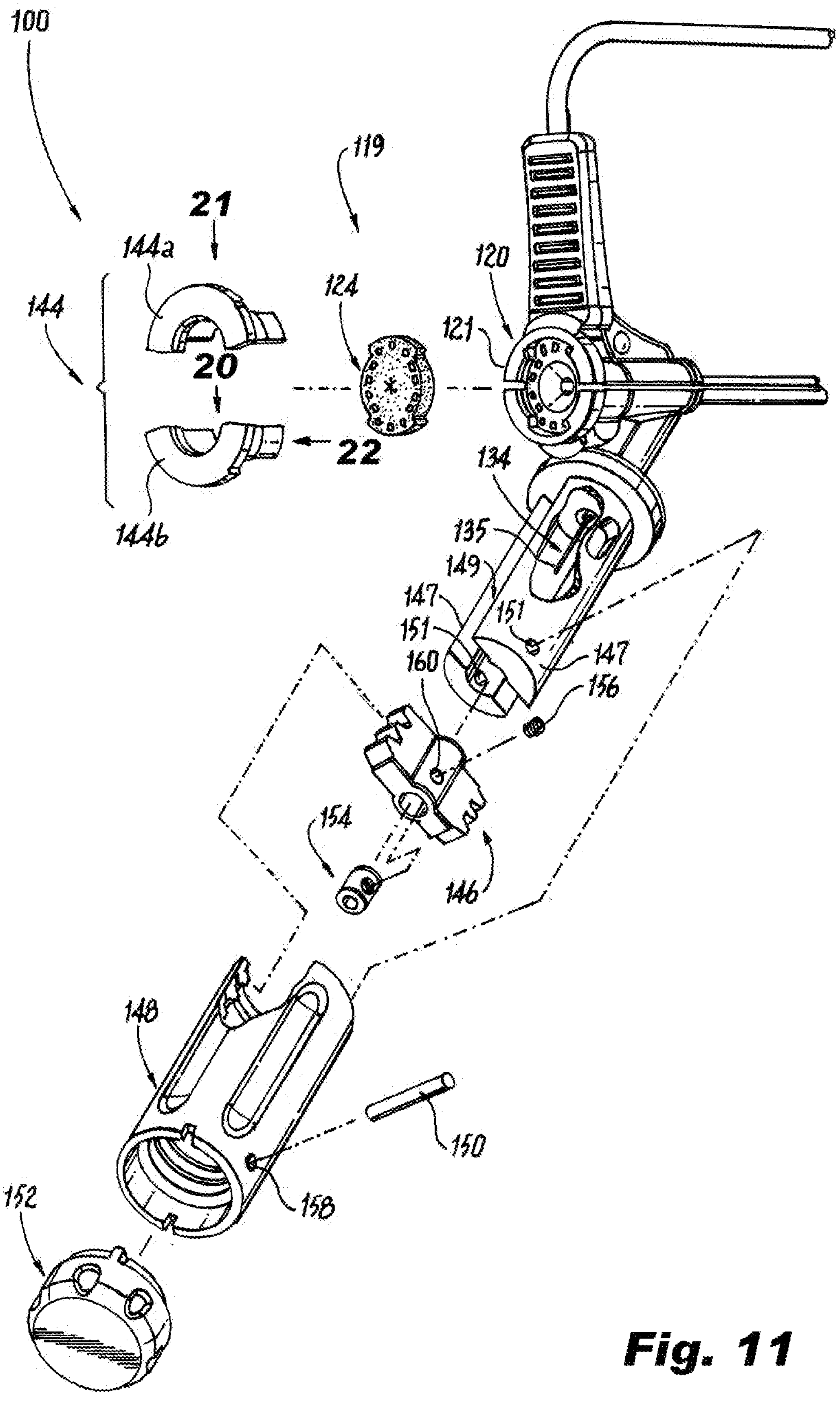
FIG. 11 is a perspective partially exploded view of the proximal end portion of FIG. 6, showing the components of one of the spreadable handles, the hub, and the hemostatic valve.
Figure 12:
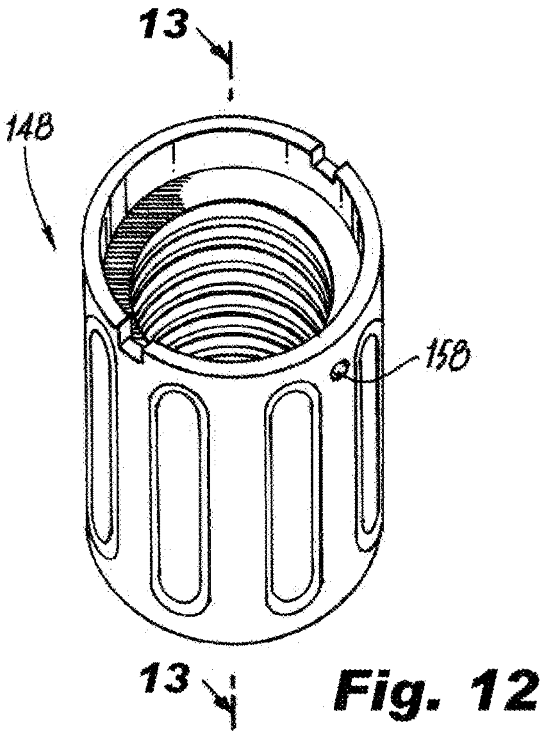
FIG. 12 is perspective view of a rotator knob of one of the spreadable handles, showing threads on the inner surface.
Figure 13:
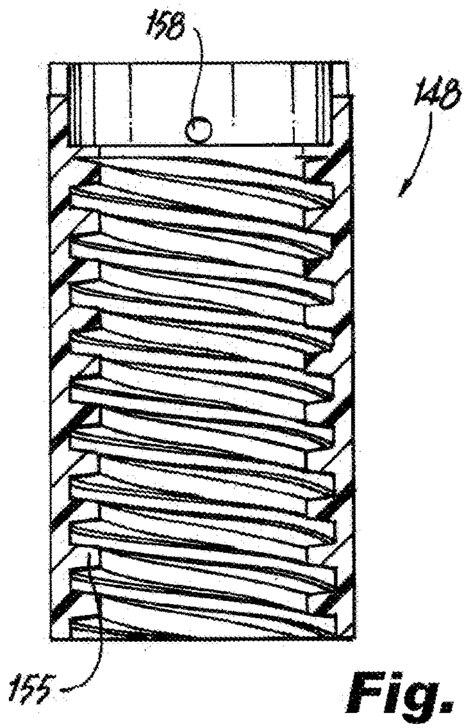
FIG. 13 is a schematic cross section view of the rotator knob of FIG. 12, showing the threads and a locking pin entry hole.
Figure 14:
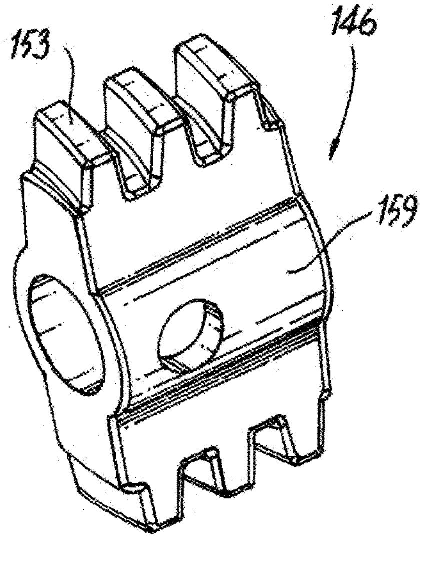
FIG. 14 is a perspective view of a pull wire actuator placed within the rotator knob of FIG. 13, showing the corresponding threads lining up with those on the inner surface of the rotator knob.
Figure 15:
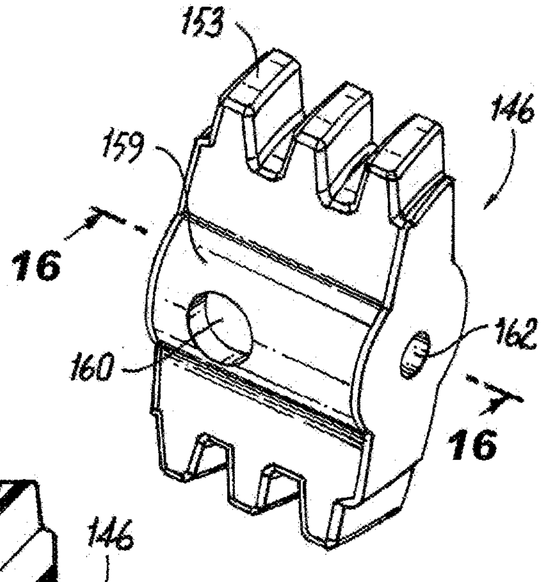
FIG. 15 is a perspective view of the pull wire actuator of FIG. 14, showing a hole for an Allen key wrench.

As shown in FIG. 11, the hub 120 along with the hemostatic valve 124 and a hub cap 144 form a hub assembly 119. The hub cap 144 secures hemostatic valve 124 in place on the hub 120. The spreadable rotating twist deflection handle 114 further includes two spaced apart arms 147 extending from hub 120 forming a longitudinal guide slot 149 therebetween. Bach arm 147 has a curved interior surface 157. The spreadable rotating twist deflection handle 114 includes pull wire actuator 146 configured and adapted to slide along the curved interior surfaces 157 within longitudinal guide slot 149. Each arm 147 includes a locking pin hole 151 for receiving a locking pin 150. The spreadable rotating twist deflection handle 114 includes a rotatable deflection knob 148 with an entry hole 158 for locking pin 150. Entry hole 158 is used to allow entry of locking pin 150 to engage with locking pin holes 151. Once pin 150 is within holes 151, the pin 150 clears the inner diameter of rotatable deflection knob 148 such that rotatable deflection knob 148 is able to rotate about arms 147.

Figure 16:
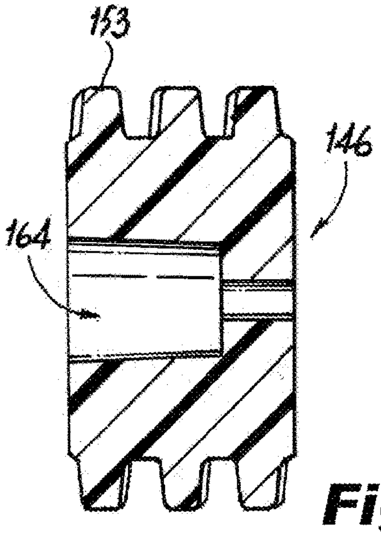
FIG. 16 is a schematic cross sectional side view of the pull wire actuator of FIG. 14, showing a hollow space for receiving the pull wire anchor.
Figure 17:
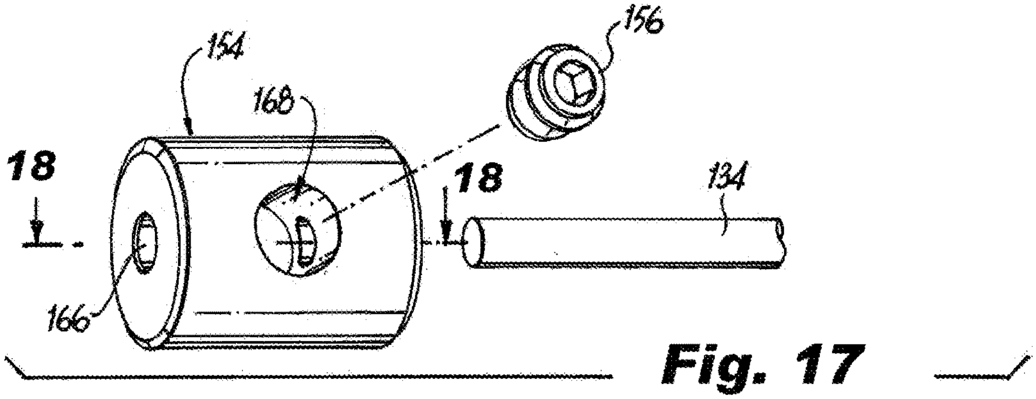
FIG. 17 is an exploded perspective view of a pull wire anchor assembly for placing within the pull wire actuator of FIG. 14, showing a set screw, proximal end of the pull wire, and receiving hole of the pull wire anchor.

With continued reference to FIG. 11, spreadable rotating twist deflection handle 114 includes a rotator knob cap 152, a pull wire anchor 154 with a hole 166 for the entry of pull wire 134, and a set screw 156. The rotatable deflection knob 148 is operatively connected to a proximal end 135 of a pull wire 134 via pull wire actuator 146 and pull wire anchor 154 to drive deflection of the distal end portion 106 of the elongated sheath 102, The proximal end 135 of the pull wire 134 is anchored to the pull wire actuator 146 with pull wire anchor 154. The rotatable deflection knob 148 is rotatable relative to the arms 147 and other portions of spreadable handle 114. The pull wire actuator 146 includes a hole 160 for an Allen key and an opening 162 (shown in FIG. 15) for receiving pull wire 134. As shown in FIGS. 16-17, the actuator 146 has an opening 164 for acceptance of the anchor 154.

As shown in FIG. 11-16, the actuator 146 and the rotatable deflection knob 148 each have threading. The rotatable deflection knob 148 has threads 155 covering its inner surface circumferentially, and the actuator 146 has external threading 153 so that the actuator 146 is engaged with threads 155 of the rotatable deflection knob 148. Opposed curved exterior surfaces 159 of the actuator 146 move axially back and forth longitudinally along the curved interior surfaces 157 such that the body of the actuator 146 moves axially along the longitudinal guide slot 149. That way, when rotatable deflection knob 148 is turned in a first rotational direction, clockwise or counter-clockwise, threads 155 of the rotatable deflection knob 148 engaged with the threads 153 of the actuator 146 to cause the actuator 146 to move or translate in a proximal direction along the longitudinal guide slot 149 between arms 147 and away from the hub 120, The arms 147 prevent the actuator 146 from rotating as the rotatable deflection knob 148 is rotated, instead causing the actuator 146 to only translate along the longitudinal guide slot 149. With the actuator 146 connected to proximal end 135 of the pull-wire 134 and with distal end 143 of the pull-wire 134 connected to the distal end portion 106 of the elongated sheath 102, this causes the distal end portion 106 and distal tip 110 of the sheath 102 to deflect out of axial alignment with the proximal end portion 104 of the sheath 102.

Figure 23:
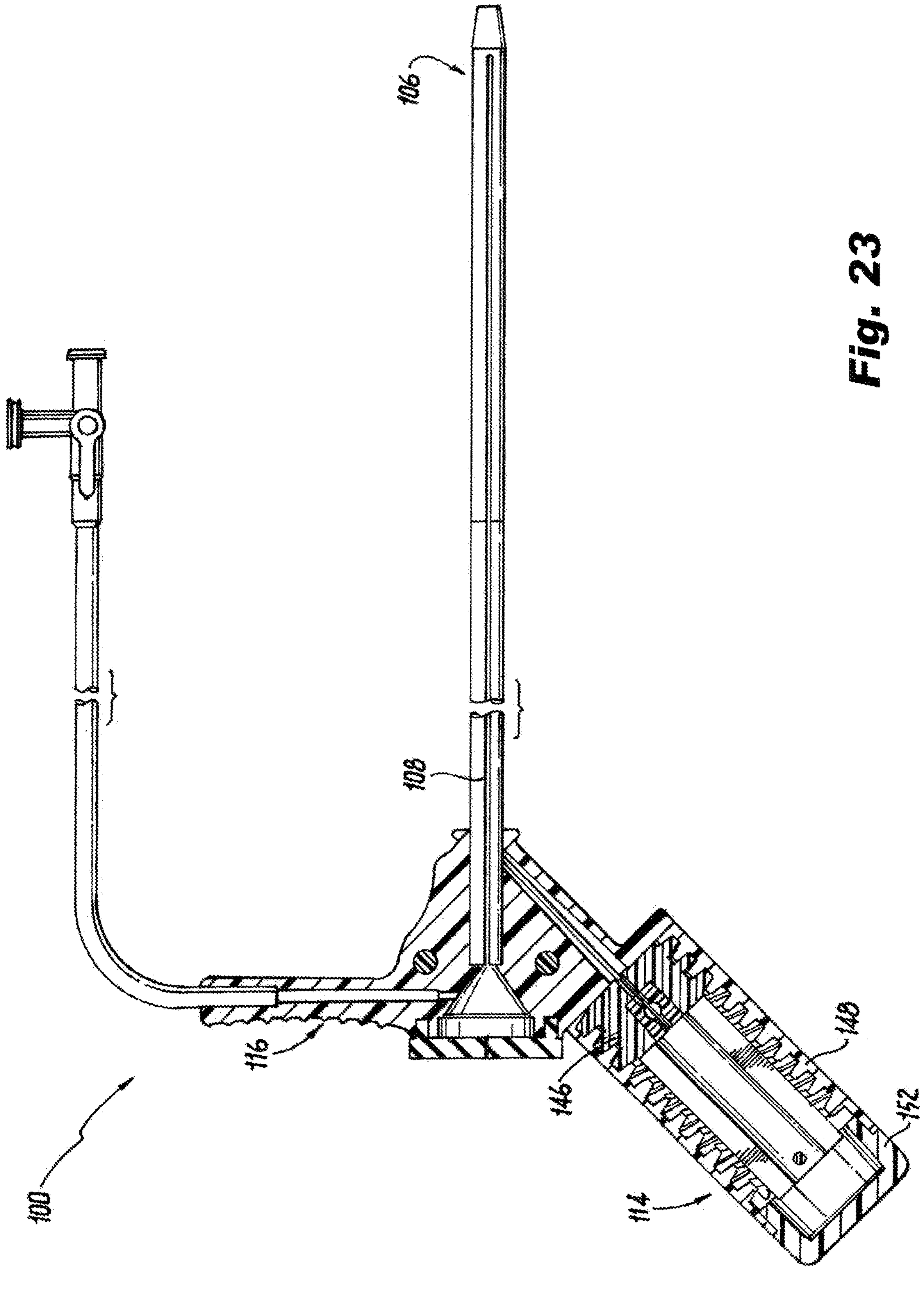
FIG. 23 is a cross section view of the deflectable vascular peel away introducer assembly of FIG. 1, showing the rotating twist deflection handle, control wire, and break away handle with the hemostatic valve when the string actuator is in the distal position.
Figure 24:
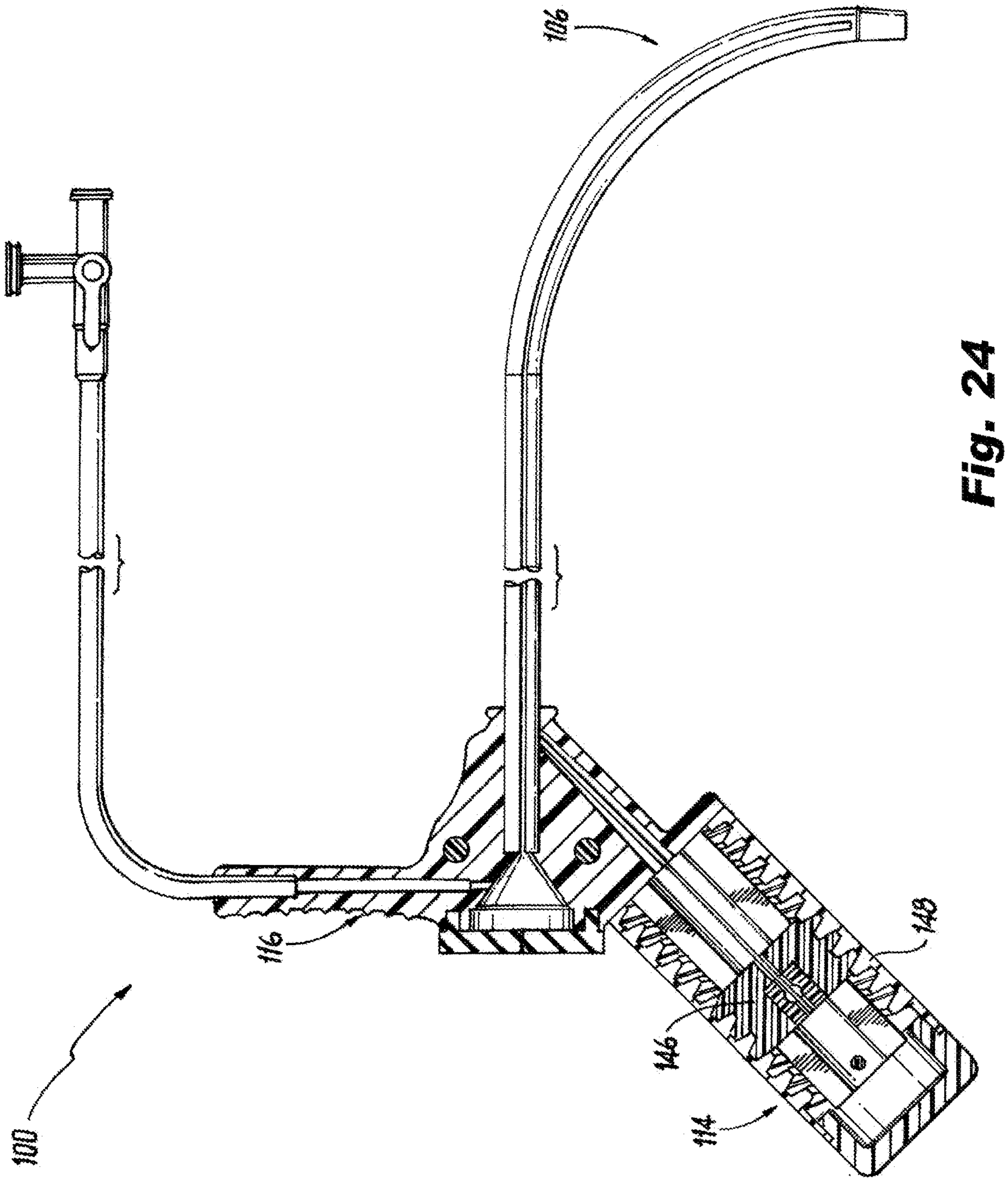
FIG. 24 is a cross section view of the deflectable vascular peel away introducer assembly of FIG. 1, showing the rotating twist deflection handle, control wire, and break away handle with the hemostatic valve when the distal end of the elongated sheath is in a deflected position.
Figure 25:
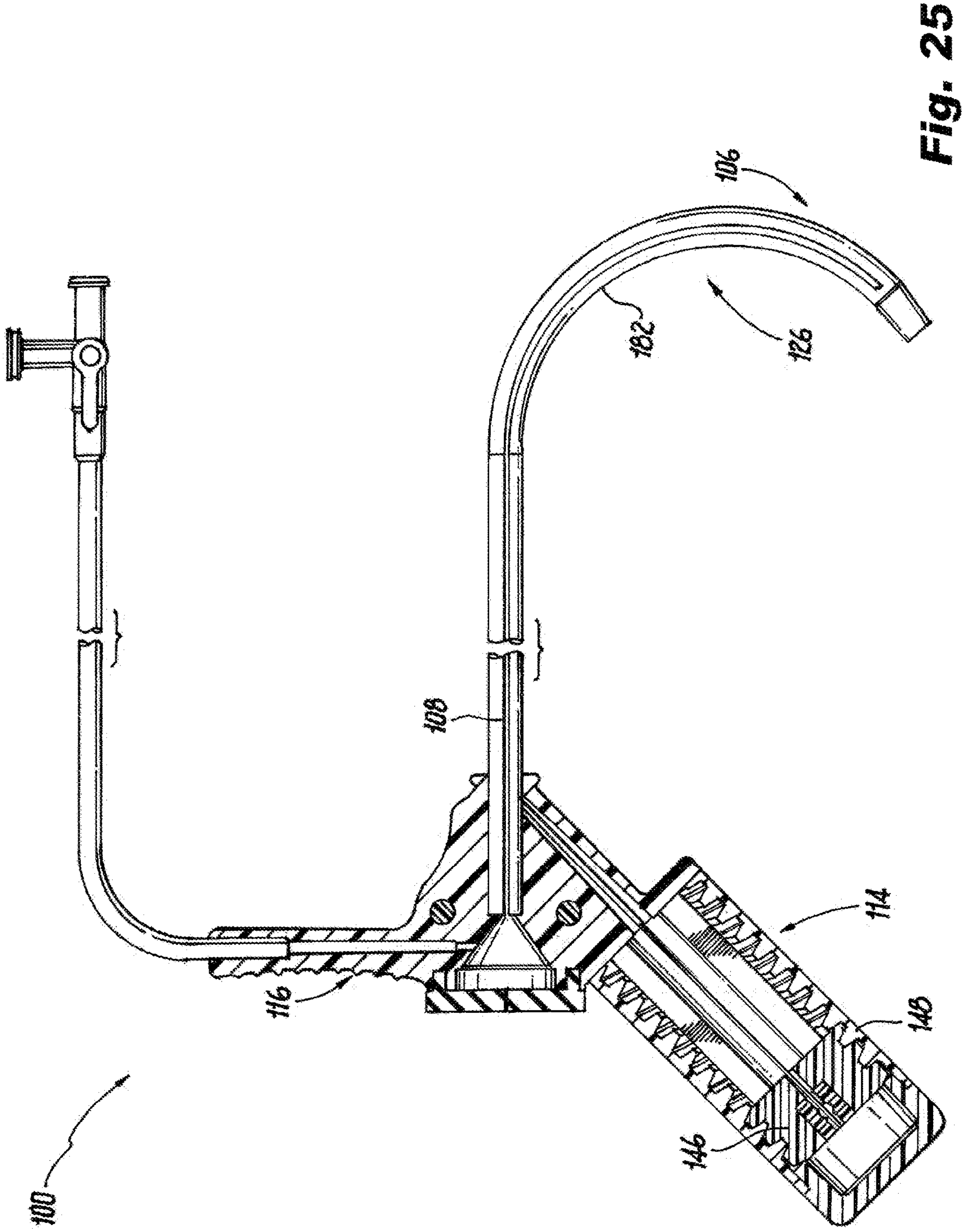
FIG. 25 is a cross section view of the deflectable vascular peel away introducer assembly of FIG. 1, showing the rotating twist deflection handle, control wire, and break away handle with the hemostatic valve when the distal end of the elongated sheath is in a further deflected position.

As shown in FIGS. 23-25, the more rotatable deflection knob 148 is rotated in the first rotational direction, the further the actuator 146 travels proximally away from the hub 120 along longitudinal guide slot 149 to thereby cause a greater deflection of the distal end portion 106 of the sheath 102. FIG. 25 shows the actuator 146 in its fully retracted position. Then, to cause the distal end portion 106 of the sheath 102 to return to its normal, undeflected position (FIG. 23), the rotatable deflection knob 148 is rotated in a second, opposite direction, either counter-clockwise or clockwise, opposite the first rotational direction. This causes the threading 155 in the rotatable deflection knob 148 to engage with the threads 153 of the actuator 146 to cause the actuator 146 to move in a distal direction along the longitudinal guide slot 149. This translational movement of the actuator 146 is from the fully retracted position shown in FIG. 25 through the intermediate position in FIG. 24 and back to its original position shown in FIG. 23 adjacent to the hub 120. With the actuator 146 in the position shown in FIG. 23, the distal end portion 106 of the sheath 102 is axially aligned with the proximal portion 104 of the sheath and with the hub 120.

Figure 18:
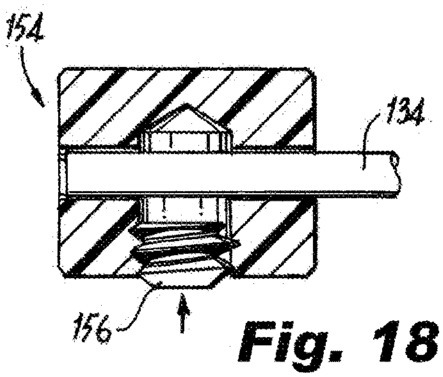
FIG. 18 is a schematic cross section view of the pull wire anchor assembly of FIG. 17, showing the set screw being inserted into the pull wire anchor to secure the pull wire to the pull wire anchor.
Figure 19:
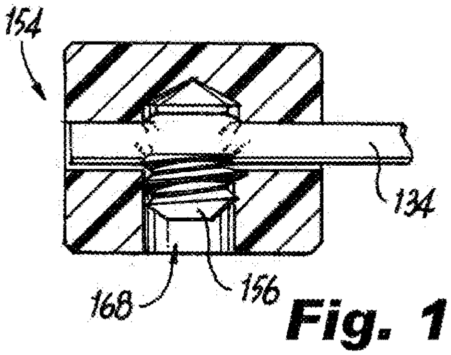
FIG. 19 is a schematic cross section view of the pull wire anchor assembly of FIG. 17, showing the set screw inserted into the pull wire anchor and securing the proximal end of the pull wire to the pull wire anchor.

With reference now to FIGS. 17-19, pull wire 134 is received within anchor 154 via a hole 166 for coupling thereto. The anchor 154 has another hole 168, opening in a direction perpendicular to that of hole 166, for the acceptance of the set screw 156. With anchor 154 received in opening 164 of actuator 146 the proximal end of the pull wire 134 is moved into opening 162 and beyond hole 168, as shown in FIGS. 18 and 19. Set screw 156 is threaded into lateral hole 168 to secure the pull-wire 134 in place inside the actuator 154. The set screw 156 acts to compress pull wire 134, thereby mechanically coupling pull wire 134 inside anchor 154, in turn housed inside the opening 164 of actuator 146.

Figure 20:
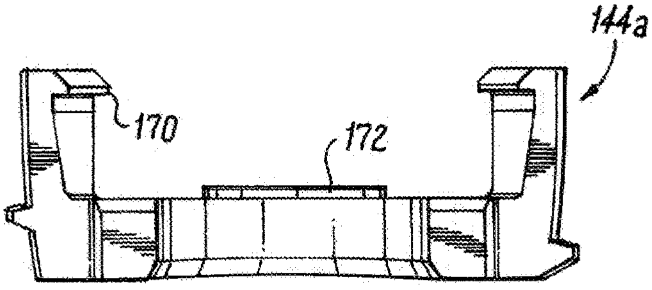
FIG. 20 is a side elevation view of one half of the hub cap of the deflectable vascular peel away introducer assembly of FIG. 1, showing an inner surface of the hub cap and snap hooks for securing onto the hub.
Figure 21:
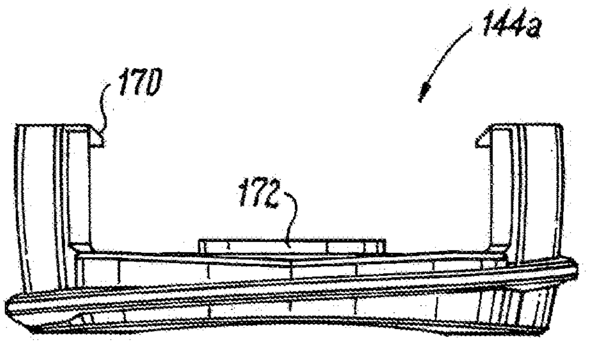
FIG. 21 is a side elevation view of one half of the hub cap of the deflectable vascular peel away introducer assembly of FIG. 1, showing an outer surface of the hub cap and a thread for engaging with a dilator hub lock nut.
Figure 22:
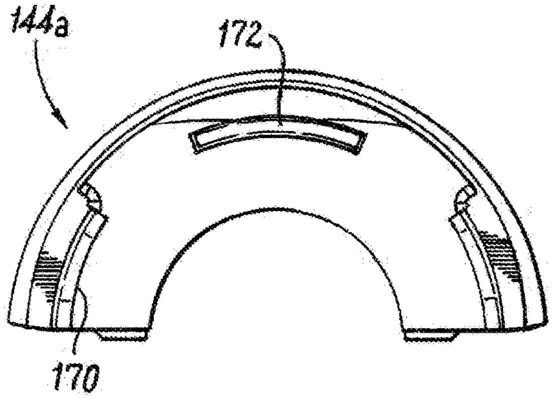
FIG. 22 is bottom elevation view of one-half of the hub cap of the deflectable vascular peel away introducer assembly of FIG. 1, showing the valve depressor.

With reference now to FIGS. 20-22, one-half **144*a* of hub cap 144 is shown. Each hub half 144*a*, 144*b* is identical to the other and each snaps onto opposing sides of a proximal end 121 of hub 120. Hub half 144*a* includes two snap hooks 170 to secure the hub cap 144 to a proximal end 121 of hub 120. Hub half 144*a* also includes a valve depressor 172 for compressing at least a portion of hemostatic valve 124 onto hub 120. As shown in FIG. 21, hub half 144*a* contains threads for a dilator hub lock nut 123 of dilator 131**.

As shown in FIGS. 23-25, a method for deflecting and removing a vascular peel away introducer assembly, e.g., vascular peel away introducer assembly 100, includes turning a deflection knob, e.g., rotatable deflection knob 148, which causes deflection of a softer distal end portion, e.g., the softer distal end portion 106, of an elongated sheath, e.g., the elongated sheath 102, along a primary curve, e.g., the primary curve 126. The deflection can be 45 degrees or more.

More, specifically, turning deflection knob in a first rotational direction, clockwise or counter-clockwise, causes a threaded actuator, e.g. threaded actuator 146, to move proximally away from a hub, e.g. hub 120, along a longitudinal guide slot, e.g. longitudinal guide slot 149, causes deflection of the softer distal end portion. Further turning of the deflection knob in the first rotational direction causes further proximal travel of the actuator away from the hub along the longitudinal guide slot into a fully retracted position (FIG. 25) to thereby cause a greater deflection of the distal end portion of the elongated sheath. Then, to cause the distal end portion of the elongated sheath to return to its normal, undeflected position (FIG. 23), the method includes turning the deflection knob in a second, opposite direction, either counter-clockwise or clockwise, opposite the first rotational direction. This causes the actuator to move in a distal direction along the longitudinal guide slot.

Figure 26:
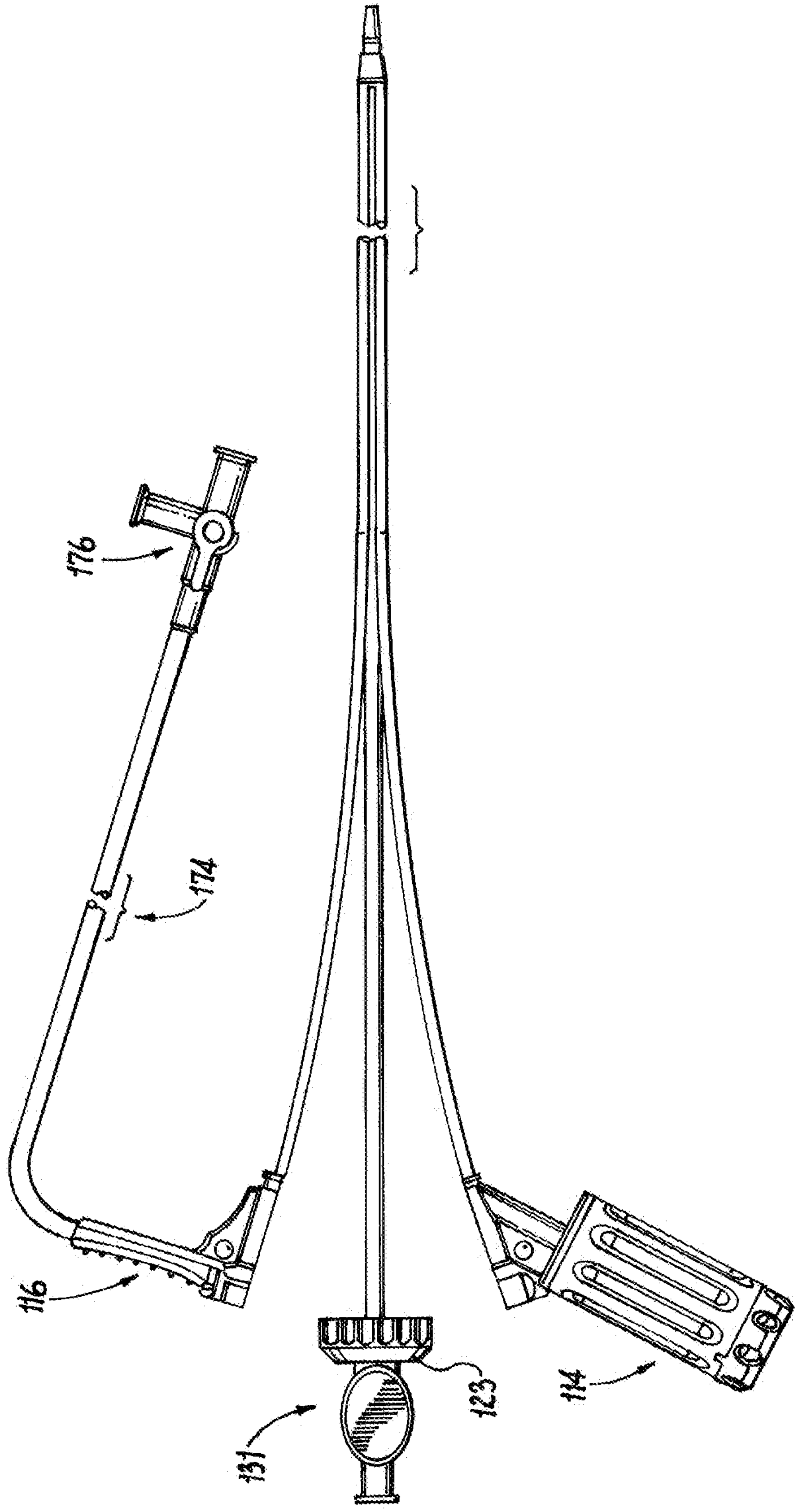
FIG. 26 is a side elevation view of the deflectable vascular peel away sheath introducer of FIG. 1, showing the two spreadable handles and elongated sheath being separated.

With reference now to FIG. 26, the method includes splitting spreadable handles, e.g. spreadable handles 114, 116, and hub, e.g. hub 120, along lines of weakness, e.g., hub lines of weakness 122, at a proximal end portion 104 of the elongated sheath. Splitting the spreadable handles facilitates separating the elongated sheath along lines of weakness, e.g., lines of weakness 108.

The methods and systems of the present disclosure, as described above and shown in the drawings, provide for a vascular peel away introducer assembly with superior properties including easy deflection and navigability, efficient fabrication, and reliable, adequate separation. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A deflectable vascular introducer, comprising:

a) an elongated sheath comprising opposed proximal and distal end portions extending along a longitudinal axis, wherein at least two axial lumens extend through the sheath;

b) a movable pull-wire positioned within one of the at least two axial lumens in the sheath, wherein the pull-wire extends from a pull wire proximal portion to a pull wire distal portion anchored to the distal end portion of the elongated sheath;

c) a hub positioned at the proximal end portion of the sheath; and d) a proximal handle assembly connected to the hub, the proximal handle assembly comprising a breakaway spreadable handle opposite a spreadable rotating twist deflection handle, wherein the spreadable rotating twist deflection handle comprises:

i) a pair of spaced apart first and second hub arms extending proximally from the hub, the first and second hub arms each comprising first and second curved exterior surfaces meeting respective first and second planar interior surface, wherein the first and second planar interior surfaces have respective first and second interior curved surfaces facing each other to form a longitudinal guide slot;

ii) a pull wire actuator disposed in the longitudinal, guide slot and comprising a cylindrically shaped central actuator portion supporting opposed outwardly extending first and second actuator arms provided with external threads, wherein the central actuator portion has a longitudinally extending central actuator opening comprising a proximal central actuator opening of a first diameter extending partway along the actuator in open communication with a distal central anchor opening of a second diameter greater than the first diameter, and wherein a lateral opening extends through the cylindrically shaped central actuator portion in open communication with the distal central actuator opening;

iii) a cylindrically shaped pull wire anchor comprising a longitudinal anchor opening that is sized to receive a proximal portion of the pull wire and a threaded lateral anchor opening that threadingly receives a set screw;

iv) a rotatable deflection knob comprising circumferential internal threads, wherein with the pull wire actuator disposed in the longitudinal guide slot between the pair of spaced-apart first and second hub arms, and with the anchor received in the distal central opening of the pull wire actuator with the proximal portion of the pull wire extending through the proximal central opening in the pull wire actuator and into the longitudinal anchor opening with the set screw threaded into the lateral anchor opening to connect the pull wire to the anchor, the anchor in turn residing in the distal central opening in the pull wire actuator, the circumferential internal threads of the rotatable deflection knob are threadingly engaged with the external threads of the opposed first and second actuator arms so that:

A) rotation of the rotatable deflection knob in one of a clockwise or counterclockwise direction causes the pull wire actuator to translate in a proximal direction along the longitudinal guide slot between the spaced-apart first and second hub arms and away from the hub to move the pull wire proximally within the one of the at least two axial lumens in the sheath to thereby cause the distal end portion of the sheath to deflect out of axial alignment with the proximal end portion of the sheath, and B) rotation of the rotatable deflection knob in the other of the clockwise or counterclockwise direction causes the pull wire actuator to translate in a distal direction along the longitudinal guide slot between the spaced-apart first and second hub arms and towards the hub to thereby cause the distal end portion of the sheath to return to its normal, undeflected position.

2. The deflectable vascular introducer of claim 1, wherein the elongated sheath includes a tubular sheath wall, and wherein the movable pull-wire positioned within the one of the at least two axial lumens is embedded within the sheath wall.

3. The deflectable vascular introducer of claim 1, wherein the movable pull-wire is anchored within the one of the at least two axial lumens in the sheath with epoxy at the distal end portion of the elongated sheath.

4. The deflectable vascular introducer of claim 1, wherein the elongated sheath includes a tubular sheath wall, and wherein a second of the at least two axial lumens in the sheath is defined within an inner diameter of the tubular sheath wall.

5. The deflectable vascular introducer of claim 1, wherein the proximal end portion of the elongated sheath is stiffer and less flexible than the distal end portion of the elongated sheath.

6. The deflectable vascular introducer of claim 5, wherein the distal end portion of the elongated sheath includes at least two softer sections with different stiffness, and wherein a first of the two softer sections is configured and adapted to be deflected to a primary curve of predetermined Deflection Curve Diameter (DCD), and wherein a second of the two softer sections is pre-shaped to a secondary curve.

7. The deflectable vascular introducer of claim 6, wherein the primary curve is longer in arc-length than the secondary curve.

8. The deflectable vascular introducer of claim 1, wherein the elongated sheath defines a predetermined usable length (UL) extending from the proximal end portion to the distal tip of the distal end portion of the sheath.

9. The deflectable vascular introducer of claim 8, wherein the UL ranges from 30 cm to 70 cm.

10. The deflectable vascular introducer of claim 1, wherein the elongated sheath includes at least two axially extending sheath lines of weakness that are diametrically opposed to one another across the elongated sheath.

11. The deflectable vascular introducer of claim 10, wherein the diametrically opposed at least two axially extending sheath lines of weakness comprise longitudinal score lines extending spaced from but parallel to the longitudinal axis of the elongated sheath.

12. The deflectable vascular introducer of claim 11, wherein the longitudinally extending score lines comprising each line of weakness are defined by a longitudinally extending narrow depth "V" opposite from one another across an inner diameter of the elongated sheath, and wherein each line of weakness further includes an axially extending detent formed in an outer diameter surface of the elongated sheath, and wherein each axially extending detent is opposite from a respective one of the longitudinally extending score lines across a sheath wall.

13. The deflectable vascular introducer of claim 1, further comprising a hemostatic valve abutting a proximal end of the hub and positioned between the breakaway spreadable handle opposite the spreadable rotating twist deflection handle.

14. The deflectable vascular introducer of claim 1, wherein the hub comprises diametrically opposed hub lines of weakness disposed between the breakaway spreadable handle opposite the spreadable rotating twist deflection handle.

15. The deflectable vascular introducer of claim 1, wherein the breakaway spreadable handle includes a side port conduit extending therefrom, the side port conduit having a two-way or three-way stop cock.

16. The deflectable vascular introducer of claim 15, wherein the side port conduit is in fluid communication with one of the at least two axial lumens in the sheath.

17. The deflectable vascular introducer of claim 1, wherein the pair of spaced-apart first and second hub arms extending distally from the hub have laterally aligned openings, and wherein a locking pin resides in the laterally aligned openings.

18. The deflectable vascular introducer of claim 1, wherein the pull wire distal portion is anchored to the distal end portion of the elongated sheath via a pull wire anchor ring.

19. The deflectable vascular introducer of claim 12, wherein a wall thickness of the elongated sheath where an apex of the narrow depth "V" meets the detent is approximately 0.003 inches.

20. The deflectable vascular introducer of claim 1, further comprising a memory wire positioned within a second of the at least two axial lumens in the sheath, wherein the memory wire is configured and adapted to assist with straightening the distal end portion of the elongated sheath after deflection out of axial alignment with the proximal end portion of the sheath.

21. A method for deflecting a deflectable vascular introducer, comprising the steps of:

a) providing a deflectable vascular introducer, comprising:

i) an elongated sheath having opposed proximal and distal end portions extending along a longitudinal axis, wherein at least one axial lumen extends through the sheath;

ii) a movable pull-wire positioned in the at least one axial lumen in the sheath, wherein the -pull-wire extends from a pull wire proximal portion to a pull wire distal portion anchored to the distal end portion of the elongated sheath;

iii) a hub positioned at the proximal end portion of the sheath; and iv) a proximal handle assembly connected to the hub, the proximal handle assembly comprising a breakaway spreadable handle opposite a spreadable rotating twist deflection handle, wherein the spreadable rotating twist deflection handle comprises:

A) a pair of spaced-apart first and second hub arms extending proximally from the hub, the first and second hub arms each comprising first and second curved exterior surfaces meeting respective first and second planar interior surface, wherein the first and second planar interior surfaces have respective first and second interior curved surfaces facing each other to form a longitudinal guide slot;

B) a pull wire actuator disposed in the longitudinal guide slot and comprising a cylindrically shaped central actuator portion supporting opposed outwardly extending first and second actuator arms provided with external threads, wherein the central actuator portion has a longitudinally extending central actuator opening comprising a proximal central actuator opening of a first diameter extending part-way along the pull wire actuator in open communication with a distal central anchor opening of a second diameter greater than the first diameter, and wherein a lateral opening extends through the cylindrically shaped central actuator portion in open communication with the distal central actuator opening;

C) a cylindrically shaped pull wire anchor comprising a longitudinal anchor opening that is sized to receive a proximal portion of the pull wire and a threaded lateral anchor opening that threadingly receives a set screw;

D) a rotatable deflection knob comprising circumferential internal threads, wherein with the pull wire actuator disposed in the longitudinal guide slot between the pair of spaced-apart first and second hub arms, and with the anchor received in the distal central opening of the pull wire actuator with the proximal portion of the pull wire extending through the proximal central opening in the pull wire actuator and into the longitudinal anchor opening with the set screw threaded into the lateral anchor opening to connect the pull wire to the anchor, the anchor in turn residing in the distal central opening in the pull wire actuator, the circumferential internal threads of the rotatable deflection knob are threadingly engaged with the external threads of the opposed first and second actuator arms so that:

b) rotating the rotatable deflection knob in one of a clockwise or counterclockwise direction causes the pull wire actuator to translate in a proximal direction along the longitudinal guide slot between the spaced-apart first and second hub arms and away from the hub to move the pull wire proximally within the at least one axial lumen in the sheath to thereby cause the distal end portion of the sheath to deflect out of axial alignment with the proximal end portion of the sheath, and c) rotating of the rotatable deflection knob in the other of the clockwise or counterclockwise direction causes the pull wire actuator to translate in a distal direction along the longitudinal guide slot between the spaced-apart first and second hub arms and towards the hub to thereby cause the distal end portion of the sheath to return to its normal, undeflected position.

22. The method of claim 21, further including:

a) providing the sheath having at least two diametrically opposed axially extending sheath lines of weakness extending spaced from but parallel to the longitudinal axis of the elongated sheath;

b) providing the hub comprising diametrically opposed hub lines of weakness disposed between the breakaway spreadable handle opposite the spreadable rotating twist deflection handle; and c) splitting the deflectable vascular introducer along the hub lines of weakness and the sheath lines of weakness.

23. A deflectable vascular introducer, comprising:

a) an elongated sheath comprising opposed proximal and distal end portions extending along a longitudinal axis, wherein at least one axial lumen extends through the sheath;

b) a movable pull-wire positioned within the axial lumen in the sheath, wherein the pull-wire extends from a pull wire proximal portion to a pull wire distal portion anchored to the distal end portion of the elongated sheath;

c) a hub positioned at the proximal end portion of the sheath; and d) a proximal handle assembly connected to the hub, the proximal handle assembly comprising a breakaway spreadable handle opposite a spreadable rotating twist deflection handle, wherein the spreadable rotating twist deflection handle comprises:

i) a pair of spaced-apart first and second hub arms extending proximally from the hub, the first and second hub arms each comprising first and second curved exterior surfaces meeting respective first and second planar interior surface, wherein the first and second planar interior surfaces have respective first and second interior curved surfaces facing each other to form a longitudinal guide slot;

ii) a pull wire actuator disposed in the longitudinal guide slot and comprising a cylindrically shaped central actuator portion supporting opposed outwardly extending first and second actuator arms provided with external threads, wherein the central actuator portion has a longitudinally extending central actuator opening comprising a proximal central actuator opening of a first diameter extending part-way along the actuator in open communication with a distal central anchor opening of a second diameter greater than the first diameter, and wherein a lateral opening extends through the cylindrically shaped central actuator portion in open communication with the distal central actuator opening;

iii) a cylindrically shaped pull wire anchor comprising a longitudinal anchor opening that is sized to receive a proximal portion of the pull wire and a threaded lateral anchor opening that threadingly receives a set screw;

iv) a rotatable deflection knob comprising circumferential internal threads, wherein with the pull wire actuator disposed in the longitudinal guide slot between the pair of spaced-apart first and second arms, and with the anchor received in the distal central opening of the pull wire actuator with the proximal portion of the pull wire extending through the proximal central opening in the pull wire actuator and into the longitudinal anchor opening with the set screw threaded into the lateral anchor opening to connect the pull wire to the anchor, the anchor in turn residing in the distal central opening in the pull wire actuator, the circumferential internal threads of the rotatable deflection knob are threadingly engaged with the external threads of the opposed first and second actuator arms so that;

A) rotation of the rotatable deflection knob in one of a clockwise or counterclockwise direction causes the pull wire actuator to translate in a proximal direction along the longitudinal guide slot between the spaced-part first and second hub arms and away from the hub to move the pull wire proximally within the at least one axial lumen in the sheath to thereby cause the distal end portion of the sheath to deflect out of axial alignment with the proximal end portion of the sheath, and B) rotation of the rotatable deflection knob in the other of the clockwise or counterclockwise direction causes the pull wire actuator to translate in a distal direction along the longitudinal guide slot between the spaced-apart first and second hub arms and towards the hub to thereby cause the distal end portion of the sheath to return to its normal, undeflected position.

* * * * *